United States Patent [19]
Openiano

[11] Patent Number: 5,139,261
[45] Date of Patent: Aug. 18, 1992

[54] FOOT-ACTUATED COMPUTER GAME CONTROLLER SERVING AS A JOYSTICK

[76] Inventor: Renato M. Openiano, P.O. Box 45156, San Diego, Calif. 92145

[21] Appl. No.: 761,484

[22] Filed: Sep. 18, 1991

Related U.S. Application Data

[63] Continuation-in-part of Ser. No. 626,671, Dec. 12, 1990, Pat. No. 5,076,584, which is a continuation-in-part of Ser. No. 407,468, Sep. 15, 1989, abandoned.

[51] Int. Cl.$^5$ .......................... A63F 9/00; A63B 23/00
[52] U.S. Cl. ................... 273/148 B; 273/438; 482/4; 482/908
[58] Field of Search .............. 273/148 B, 433, 434, 273/438, DIG. 28, 85 G, 440, 446, 454; 272/70, 96, 100, 129, DIG. 4, DIG. 9; 364/410; 340/709, 323 R; 200/61.1, 86.5, DIG. 23

[56] References Cited

U.S. PATENT DOCUMENTS

| | | | |
|---|---|---|---|
| 3,834,702 | 9/1974 | Bliss | 273/86 B |
| 4,278,095 | 7/1981 | Lapeyve | 273/438 |
| 4,488,017 | 12/1984 | Lee | 273/438 |
| 4,512,567 | 4/1985 | Phillips | 273/148 B |
| 4,558,864 | 12/1985 | Medwedeff | 273/148 B |
| 4,630,817 | 12/1986 | Buckley | 273/438 |
| 4,720,789 | 1/1988 | Hector et al. | 273/438 |
| 4,817,950 | 4/1989 | Goo | 273/148 B |
| 4,925,189 | 5/1990 | Braeunig | 273/148 B |

Primary Examiner—Paul E. Shapiro
Assistant Examiner—Jessica J. Harrison
Attorney, Agent, or Firm—William C. Fuess

[57] ABSTRACT

A controller electrically interfaced to a video game computer or the like for the purpose of controlling a progression of the video game or the like is selectively actuated by discrete motions and forces the locations, magnitudes, and orientations of which are variably predetermined by the user. Pressure, or proximity, sensor units, normally four in number, are independently placeable upon any surface, and normally upon a floor. The signals produced by the arbitrarily located pressure or proximity sensors are received by a video game control unit and used to produce electrical signals suitable to be received by a conventional video game computer or the like for the purpose of controlling the progression of the video game. An adjustable sensor cartridge assembly for use with a video game controller allows a user to selectively position the sensor within the collar's cavity and relative to the human user. Because the spatial arrangements of the various sensors, and the selection of the forces to be applied thereto, are completely arbitrary, the user is in complete control of the nature and location and magnitude of those motions and forces that he or she must provide, at a preselected degree of difficulty, to the game controller in order to sequence the video game.

11 Claims, 7 Drawing Sheets

FOOT-ACTUATED COMPUTER GAME CONTROLLER SERVING AS A JOYSTICK

REFERENCE TO RELATED PATENT APPLICATIONS

The present patent application is a continuation-in-part of U.S. patent application Ser. No. 626,671 filed Dec. 12, 1990 for a COMPUTER GAME CONTROLLER WITH USER-SELECTABLE ACTUATION, now U.S. Pat. No. 5,076,584 which is a continuation-in-part of U.S. patent application Ser. No. 407,468 filed Sep. 15, 1989 for a FOOT CONTROLLED COMPUTER GAME CONTROLLER WITH DETACHABLE WEIGHT HAND SWITCHES, now abandoned.

FIELD OF THE INVENTION

The present invention generally concerns computer game controllers and exercise equipment controllers, and particularly controllers that are suitably actuated in various manners, including by the feet, for the control of computer games and exercise equipments. More specifically, this invention concerns user-adjustable sensor cartridge assemblies for use with video game controllers to selectively position sensors within the assembly housing and relative to the human user, giving the user control over the degree of exertion.

BACKGROUND OF THE INVENTION

There exist many different types of controllers for computer games, or exercise equipments, or the like. The controllers are selectively actuated by a human user to produce a signal input which the computer game, or exercise equipment, will use to produce a desired effect. These controllers—especially if intended for use with computer games or exercise equipments that elicit user-generated physical forces and/or agile motions for controller actuation—generally predetermine (i) the nature, (ii) the location(s), and (iii) the magnitude, of the forces and motions that must be generated by the user and applied to the controller.

For example, U.S. Pat. No. 3,834,702 for a JOGGING GAME APPARATUS shows a mat upon which a user jogs in place in order to establish, and control, a simulated race on a game board between a game piece representing the user and a simulated competitive runner. The pace of the jogging is important for the user to win the race, but the magnitude or force of the user-generated jogging motion is not sensed, and the location of the user-generated jogging motion is predetermined.

U.S. Pat. No. 4,278,095 for an EXERCISE MONITOR SYSTEM AND METHOD shows an exerciser, such as a treadmill for running or an equivalent device for simulated cycling or rowing or the like, that is powered by the user. The user's speed, and progress, is interactive with the monitoring device, and system, so as to change the speed of an outdoors exercising scene that is presented to the user. Though the user may control the magnitude, and pace, of his/her exercise, the fundamental nature of the type of exercise motions—either walking, or jogging, or rowing, etc.— that the user must supply in order to actuate the monitor system is predetermined. Additionally, the system is interactive with the user, monitoring the user to control the pace of presentations. This type of interactive presentation control is impractical for standard video tapes which run at a fixed and invariant speed on VCRs.

U.S. Pat. No. 4,488,017 for a CONTROL UNIT for video games and the like shows control units actuated by both the hands and feet. The necessary actuation stimuli is, however, predetermined.

U.S. Pat. No. 4,512,567 for an EXERCISE BICYCLE APPARATUS PARTICULARLY ADAPTED FOR CONTROLLING VIDEO GAMES shows an exercise bicycle providing control signals based on the motion of the handlebars as well as on the speed at which the bicycle is pedalled. Although the rate, and type, of the actuating motion provided by the user to control the video game may, accordingly, be varied, the fundamental nature of the physical motions that must be undergone by the user in order to control the game are predetermined by the construction of the apparatus, and are neither user selectable nor user selected.

U.S. Pat. No. 4,558,864 for a HAND GRIP EXERCISING, COMPUTER GAME CONTROLLER shows a spring-loaded hand grip device producing a variable electrical signal in proportion to the force of actuation applied thereto. The signal that is generated in proportion to applied force—which force simulates throwing or hitting or kicking—is predetermined by the preset magnitude of the spring of the hand grip.

U.S. Pat. No. 4,630,817 for a RECREATIONAL APPARATUS again shows a device, similar to the EXERCISE BICYCLE APPARATUS of U.S. Pat. No. 4,512,567, wherein substantial muscular exertion is required by an operator during the controlled play of a video game. Although the user can, by adjusting a resistance in the form of a spring, variably determine the magnitude of the force that must be applied to a cycling apparatus in order to actuate the video game, the user cannot vary the essential cycling nature of this applied force, nor the spatial dimensions of the cycling apparatus by which the force will be applied.

U.S. Pat. No. 4,720,789 for a VIDEO EXERCISER GAME FLOOR CONTROLLER WITH POSITION INDICATING FOOTPADS shows a floor controller using weight-sensitive pads. The pads occupy fixed positions, and are actuated in accordance with predetermined forces.

U.S. Pat. Nos. 4,787,624 and 4,801,137 do not concern video controllers at all, but do reveal that it is useful to an exercising user to be able to vary the weight of handles, or hand straps, that are used during physical exercises such as jumping rope.

Finally, U.S. Pat. No. 4,925,189 for a BODY-MOUNTED VIDEO GAME EXERCISE DEVICE shows a video game controller, attachable to the user's upper body, that is actuated by the leaning, bending, or other tilting of the user's upper body. A hand-held push button is attached to the controller via a flexible cord for additional control of the video game, such as the control of simulated firing.

The many previous controllers collectively indicate that it is desirable to allow a user to control different computer games, and to respond to different exercise regimens, by physically generating diverse motions and forces, at diverse rates and magnitudes, to a controller of the computer game or exercise equipment. Although the individual controllers span many different types of user-generated motions and forces, and occasionally permit the rates, or the magnitudes, of the required motion and force inputs to the controller to be preselected by the user, the individual game controllers are, in general, rigid in prescribing the nature and the location(s) of the motions and forces that the user must provide in order to satisfy the requirements of the game or exercise regimen.

Those controllers, or control systems, that permit the greatest flexibility in selecting among user-generated actuating motions and forces are often custom systems. These custom, interactive, controllers are unsuitable for the control of diverse standard computer games or video exercises where only a few simple signals (e.g., up, down, left, right, go (fire), or stop (don't fire)) control the progress, or score, within the game or exercise.

In certain videotaped exercise regimens and computer games it is desired to induce the user to undergo gross physical motions—jumping, hopping, reaching, forcibly contacting, etc.—in order to demonstrate, and to improve, his/her skill or fitness in controlling progress, and/or in obtaining a score, on the game or exercise. In these physical-type games and exercises it would be useful if users of differing physical fitness and energy levels were able to selectively, and variably, configure and reconfigure a universal controller so that a given game, or exercise, would accept different, variably predetermined, user-generated motions and forces in order to produce the same results. The user would desirably be able to preselect a universal computer game or exercise equipment controller in any of the (i) nature (ii) magnitude, or (iii) rate of the motions and forces that he/she will subsequently provide to the controller in order to register a certain level of progress, or score, on the computer game or on the exercise.

For example, advanced or physically fit users would be able to set up such a universal video exercise equipment, or computer game, controller so that it would subsequently require relatively more exacting, or more extensive, or more forceful, user-generated actuating motions and forces in order to accomplish the same results of play, or exercise, that less-advanced users could achieve by less aggressive actuation of the same controller, alternatively initialized. For example, the same user could preselect that same progress, or score, on a computer game that was at one session to be based on his or her agile movement of the legs and feet, would, at another session, be based on forceful strikes by the hands. Of course, if a particular computer game or exercise video were to suggest a certain manner of physical response—such as, for example, running and leaping—to which the user desired to adhere during play or exercise, it should be straightforward for the user to initialize and preselect the universal controller so that it will respond to the desired motions and forces.

In such a manner a controller universally user-configured in the motions and forces to which it responds might be variably customized to the requirements of individual users. It might be altered over time as an individual user either developed in strength or prowess, or desired a change in the nature of the physical motions and forces which he or she provides in order to actuate the computer game or exercise equipment. The set up, and the subsequent manual actuation, of such a variably configured controller would desirably be totally without effect on the computer game, or the exercise equipment (including VCRs playing predetermined exercise videotapes). The computer game, or exercise equipment, or videotape exercise, would proceed normally regardless of how an individual user variably configured his controller in any of the nature, magnitude, or rate of the motions and forces which he/she will provide.

SUMMARY OF THE INVENTION

The present invention contemplates a human-actuated controller, electrically interfaced to a standard video game computer or the like, that is variably user-selectable and user-selected as to the user-generated physical motions and forces that the controller will accept. The selected physical motions and forces are provided by the user to the controller for the purpose of controlling the progression, or registering a score, on a computer game or an exercise equipment or the like.

An object of this invention is a controller electrically interfaced to a video game computer or the like and usable by a human player for the purpose of controlling a progression of a video game or the like. Such a controller has a plurality of individual sensors for individually detecting the presence of a human appendage and for individually producing in response to each such detection an individually-associated detection signal.

This controller also has a substantially planar matrix for holding each of the plurality of sensors at a position selectable by the player. A video game control unit, located remotely from any one of the sensors receives the individual detection signals from individual sensors and produces electrical signals suitable to be received by the video game computer or the like, for the purpose of controlling the progression of a video game or the like.

The physical position of individual sensors may be arbitrarily predetermined, at the human's discretion, so that his/her subsequent selective actuation of sensors with his/her appendage for controlling the progression of the video game, or the like, may be rendered relatively more or less difficult, depending upon the distance of separation, and the area covered, by the sensor's positioning.

In one embodiment of the controller of this invention, the plurality of sensors is organized in an array radiating from a central point of the controller matrix. The position of individual sensors within the array of sensors may be arbitrarily altered by the human user by variably positioning the sensor within a sensor assembly housing. The pattern of placement of four sensor assemblies may be such that each pair of assemblies is radially aligned through the center point of the matrix, in opposite fashion, along its axis and the line of one pair bisects and lies perpendicularly to the line of the other pair.

In a preferred embodiment, each of the radial array of independently activatable sensor assemblies houses an independently moveable sensor. In such case, the distance of separation and the area covered relative to the human player are dependent upon user-determined axial positioning of each individual sensor unit within its housing.

An associated object of this invention, is a controller electrically interfaced to a video game computer, or the like, having a platform, the upper surface of which is relatively flat and on which a human user may suitably stand. This controller has, at its lower surface, a multiplicity of points at which a plurality of sensor housings may be individually attached.

Independently activatable sensors inside their individual housings are attachable to the lower surface of the platform at a plurality of points. This is useful for variably retaining the sensors, each at a user-selectable variable location, relative to the point of attachment, and a variable distance of separation of one sensor to the next.

A more particularly stated object of this invention is an adjustable sensor cartridge assembly for use with a video game controller comprising a sensor having a threaded central bore and actuatable by the presence of a human appendage for producing an electrical signal usable by a video game controller. This sensor is contained within an elongated collar, defining a longitudinally extending cavity located at a predetermined position relative to a human user. A threaded shaft rotatably mounted in the collar's cavity and meshing with the threads within the bore of the sensor holds the sensor in place. Rotation of the shaft causes the engaged sensor to travel axially along the shaft within the collar's cavity and to selectively position the sensor within the collar's cavity relative to the human user.

In one embodiment, the sensor cartridge contains at least one pressure sensor for detecting a pressure of greater than a threshold level as is producible by force of a human appendage.

In another embodiment, the sensor cartridge contains a proximity sensor useful for detecting a spatial proximity of a human appendage, and for producing an individually-associated detection signal in response to such a proximity detection.

These and other aspects and attributes of the present invention will become increasingly clear upon reference to the following drawings and accompanying specification.

BRIEF DESCRIPTION OF THE DRAWINGS

FIG. 3, consisting of FIG. 3a through FIG. 3h are various views, some in cut-away, of various embodiments of pressure, and proximity, switches usable in various embodiments of controllers in accordance with the present invention.

FIG. 7, consisting of FIG. 7a and FIG. 7b, shows diagrammatic representations of the plug by which the control circuit board, and controller, in accordance with the present invention, interconnects to the standard, preexisting, video game computer previously seen in FIG. 1.

DESCRIPTION OF THE PREFERRED EMBODIMENT

Figure 1:
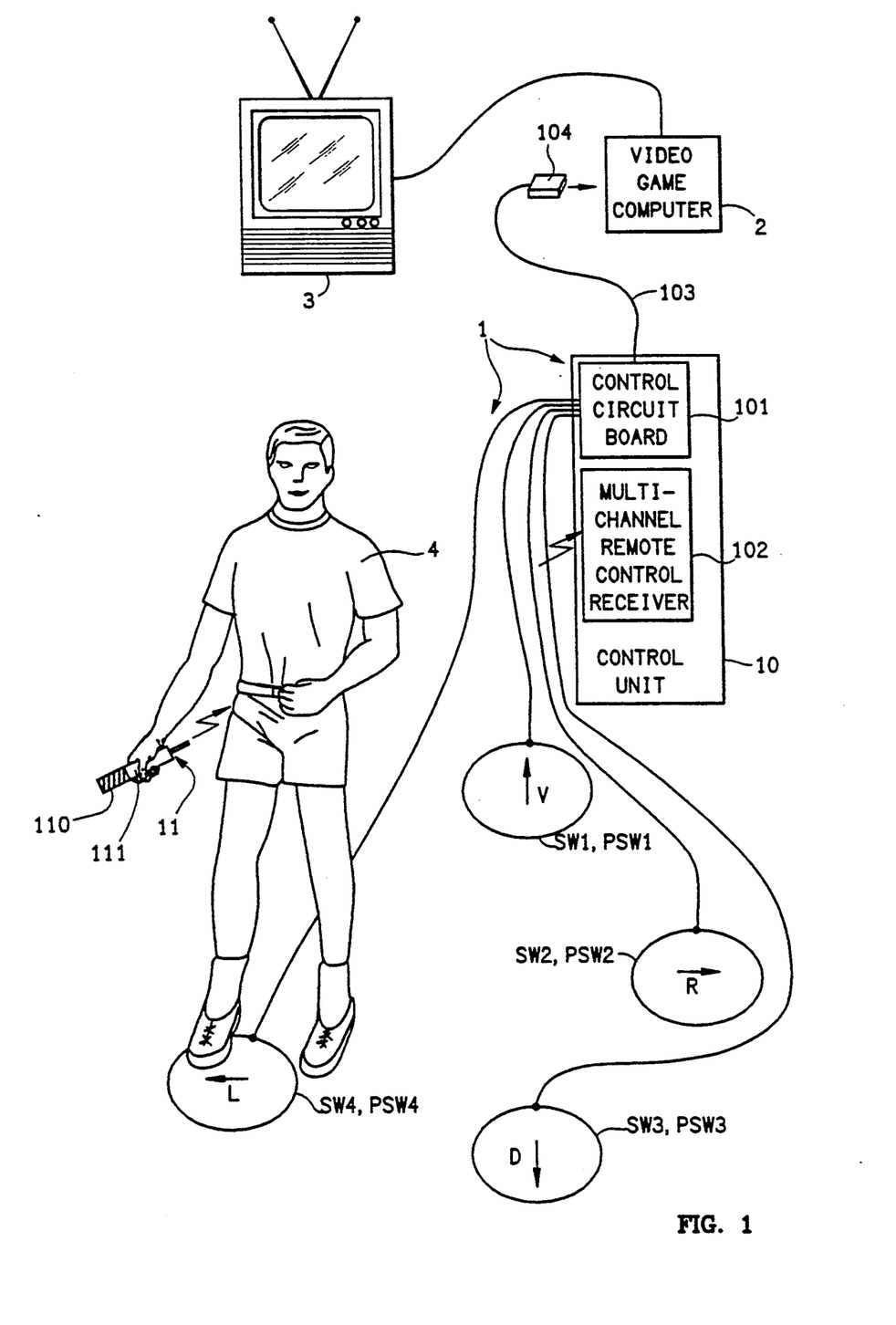
FIG. 1 is a diagrammatic representation of the preferred embodiment of a controller in accordance with the present invention arrayed in position for use by a human.

A Controller 1 in accordance with the present invention is shown in diagrammatic view in FIG. 1. The Controller 1 includes a Control Unit 10 and at least one switch SW1, or, alternatively, proximity switch PSW1. The Controller 1 normally includes four (4) pressure switches SW1–SW4, or four (4) proximity switches PSW1–PSW4. It also optionally includes a hand-held, push button switch-operated, multi-channel remote control transmitter 11.

The control unit 10 contains a CONTROL CIRCUIT BOARD 101 that typically receives signals from the switches SW1–SW4, or proximity switches PSW1–PSW4, through wires. The pressure, or proximity, switches may alternativaly communicate with the CONTROL UNIT 10, and with the control circuit board 101 therein, via wireless means, such as radio. In fact, the hand-held multi-channel remote control transmitter 11 does so communicate with the MULTI-CHANNEL REMOTE CONTROL RECEIVER 102 of the CONTROL UNIT 10 via radio. One appropriate remote transmitter-receiver pair suitable for this link is Radio Shack Part No. 277-1012. Additionally, multi-channel remote transmitter-receiver pairs are taught in the chapter titled "Experimenter's Radio Control System" appearing in "First Book of Modern Electronics" at pages 43–50, as well as in other standard references.

The control unit 10 communicates with a preexisting, standard VIDEO GAME COMPUTER 2 (shown in phantom line for not being part of the present invention) via wire 103 and plug 104. The VIDEO GAME COMPUTER 2 may particularly be the Nintendo Electronics System available from Nintendo of America, Inc., 4820 150th Avenue, NE, Redmond, Wash. 98052. Other, interface-compatible, game computers and digital control sections of exercise equipments, are as suitable for use as VIDEO GAME COMPUTER 2. The relatively simple electrical interface to the VIDEO GAME COMPUTER 2, or its equivalents, will be shown in schematic diagram of FIG. 6. In FIG. A television set 3, and a human-user 4, are also shown in phantom line for not being part of the controller 1 in accordance with the present invention.

In accordance with the principles of the present invention, the pressure switches SW1–SW4, or the alternative proximity switches PSW1–PSW4, may be located on any surface in any locations over any area. The switches are typically located on a level floor, and are arrayed so that switches varying arrows labelled "U", "R", or "L", are respectively positioned to the fore (or up), right, rear (or "down"), and left of the human user 4. The human user 4 diagrammatically illustrated in FIG. 1 would normally turn and face television 3 during actual use of the controller 1 during play of a video game under control of VIDEO GAME COMPUTER 2.

The hand-held multi-channel remote control transmitter 11 typically has added removable weight 110 positioned adjacent to the volume 111 containing the electronics, and may be selectively affixed with variable numbers of removable weights 110 in order to vary its mass, and its total weight.

Figure 2:
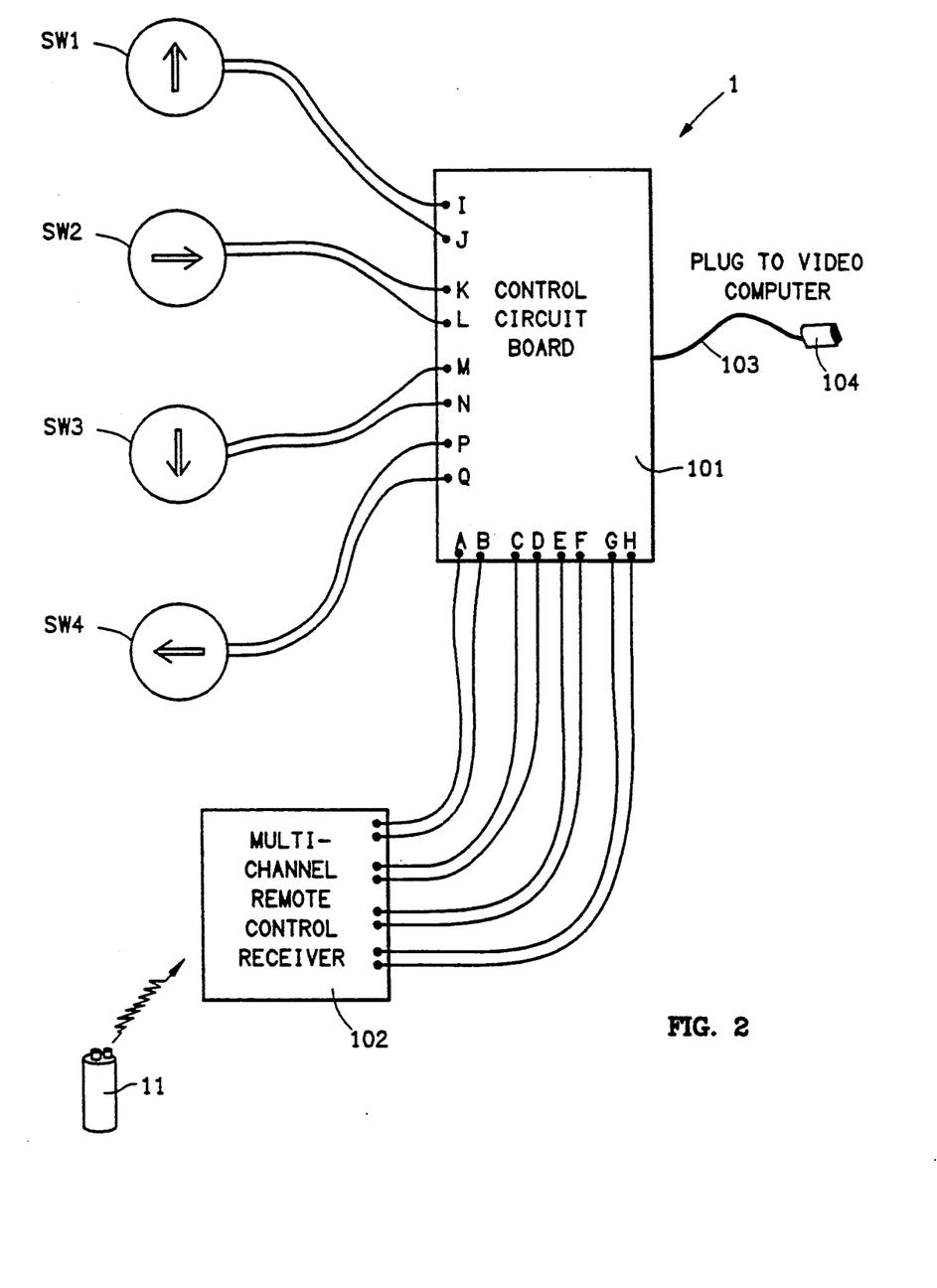
FIG. 2 is an isolated diagrammatic representation of a first embodiment of a controller in accordance with the present invention, which first embodiment uses pressure switches.

A detailed diagrammatic view of a first embodiment of the controller 1, using selectively positioned and oriented pressure switches SW1-SW4, is shown in FIG. 2. The pressure switches SW1-SW4 connect to the CONTROL CIRCUIT BOARD 101 through two (2) wires each, typically eighteen (18) gauge twisted pair wire. The pressure switches SW1-SW4 operate under pressure to produce a closed circuit connection exhibiting electrical continuity between the respective pair of pins by which each such pressure switch SW1-SW4 connects to control circuit board 101.

The hand-held multi-channel remote control transmitter 11 typically transmits up to four (4) signals in response to selective manual actuation of up to four (4) switches, typically push-button switches. These signals are received, and decoded, at MULTI-CHANNEL REMOTE CONTROL RECEIVER 102 to control electronic switches so as to establish electrical continuity between the respective wire pairs that are received at CONTROL CIRCUIT BOARD 101 as terminal pairs AB, CD, EF, and GH. The interpretation of these signal inputs is a function of the individual computer game which is connected to CONTROL CIRCUIT BOARD 101 via wire 103 and plug 104. Normally, however, at least one such switch closure represents the firing of a gun, or other action event, occurring during play of a computer game.

Thus, all signal inputs to the CONTROL CIRCUIT BOARD 101 are simply in the form of establishing an electrical closed circuit, or else an electrical open circuit, condition between an associated input terminal pair. This operation of the CONTROL CIRCUIT BOARD 101 will later be confirmed by reference to the electrical schematic shown in FIG. 6.

Figure 3A:
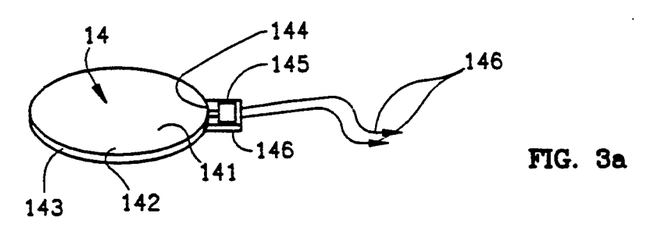

A first embodiment of a pressure switch 14 suitable for use as one of the pressure switches SW1-SW4 in the controller 1 in accordance with the present invention is shown in diagrammatic view in FIG. 3a. A top surface 141 is separated from a bottom surface 142 by a peripheral rim 143 in the form of an annular ring. A space between top surface 141 and bottom surface 142, at least one of which surfaces is flexible, establishes an air chamber. The air captive in the chamber communicates with flexible elastomeric diaphragm 144 which distends, or which retracts under elastomeric force, in accordance with whether pressure switch 14 is subject to external pressure. A conventional spring-loaded push button switch 145 is located at a variably selected position wherein it is subject to selective actuation by distention of flexible diaphragm 144. When the pressure switch 14 is subject to adequate pressure, distending the diaphragm 144, the switch 145 will close, introducing electrical continuity between leads 146 connected thereto. The physical positioning of the switch 145, which is supported by housing 146, relative to the diaphragm 144 is variable. Normal mechanical means for attachment at a variable distance may be used, including a thumb screw (not shown) manually tightened to hold the switch 145 relative to its housing 145. Accordingly, the amount of pressure that must be applied between the surfaces 141, 142 of pressure switch 14 in order to actuate the spring-loaded switch 145 is selectively variable.

Figure 3B:
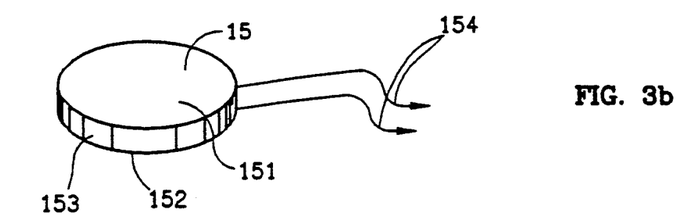

Another, more rudimentary, embodiment of a suitable pressure switch is shown as pressure switch 15 within FIG. 3b. The pressure switch 15 has an electrically conductive upper surface 151 and lower surface 152 which are normally separated by an insulating annular ring 153. Both the upper surface 151 and the lower surface 152, have a shape retentive memory, and are typically of spring steel. When appropriate pressure is applied between upper surface 151 and 152, the separating force of the annular elastomeric ring 153 is overcome, and the surfaces are pressed into momentary electrical contact. Each of the surfaces is connected to an associated one of the leads 154. Accordingly, when appropriate pressure is applied to the pressure sensor 15, electrical continuity is established for the duration of such pressure condition between leads 154.

Figure 3C:
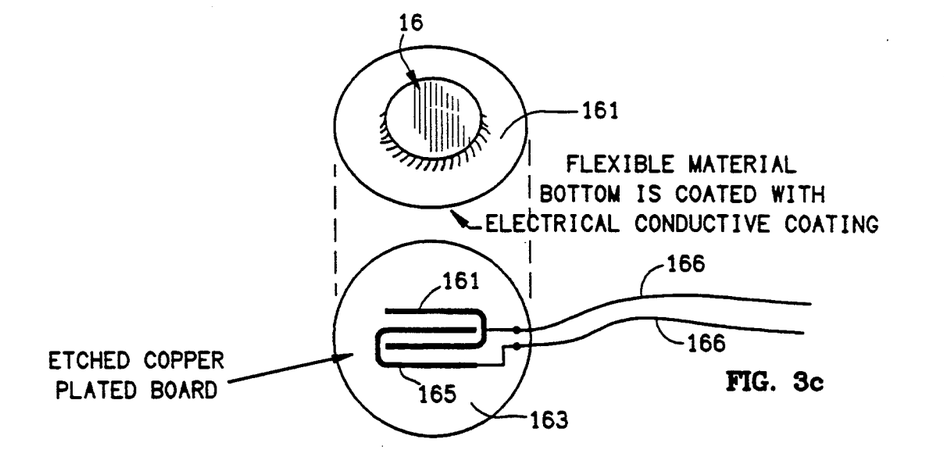
Figure 3D:
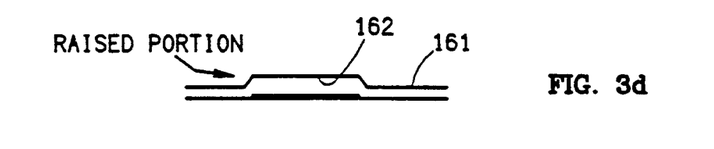

Still another pressure switch, or sensor, suitable for use in the controller 1 in accordance with the present invention is shown in exploded perspective view in FIG. 3c, and in cut-away cross-sectional view in FIG. 3d. Within this pressure switch 16, an elastomeric upper dome 161 is coated on its bottom side with electrically conductive material 162, normally copper. Meanwhile a bottom plate 163, normally of epoxy glass, is etched with two (2) electrically disconnected copper patterns 164, 165, as illustrated. Each etched copper pattern connects to a respective one of the leads 166. There is normally an electrical open condition between the two leads. However, as will be most clearly illustrated in FIG. 3d, when the flexible elastomeric upper member 161 is suitably depressed under pressure force the electrically conductive coating 162 at the under side of its raised dome will come into simultaneous contact with both of the patterns 164, 165 on the lower member 163. This electrical contact will bridge the patterns, establishing electrical continuity therebetween and between the leads 166.

Figure 3E:
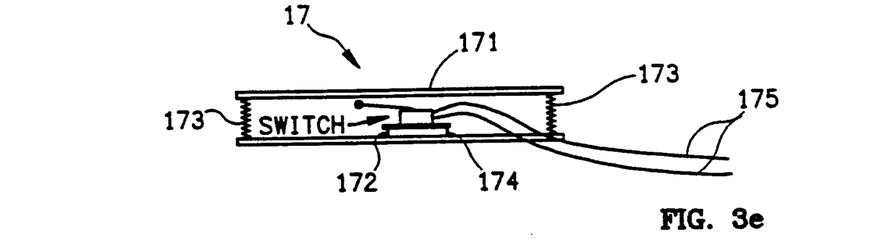

Still another, fourth, embodiment of a pressure switch suitable for use in the controller 1 in accordance with the present invention is shown in FIG. 3e. Within the pressure switch 17 and upper member 171 is held physically separated from a lower member 172 under the force of springs 173. Both the upper member 171 and the lower member 172 are typically rigid, and circular in area. A micro-switch 174 is located between the upper and lower members, and is subject to being closed, establishing continuity between leads 175 when the upper member 171 is moved proximate to lower member 172 by a pressure force that overcomes the force of springs 173.

Figure 3F:
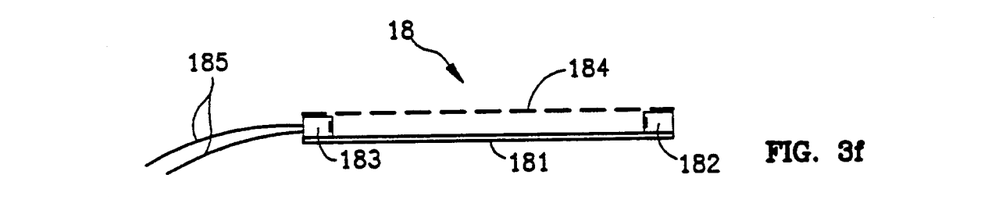

A pressure switch 18 suitable for use in the controller 1 in accordance with the present invention is shown in side cross-sectional view in FIG. 3f. A rigid base 181 supports a light source 182, normally a LED, and a light detector 183, normally a phototransistor, at spatial separation. There may be an optional upper elastomeric cover 184 to the pressure switch 18, or such cover may be omitted, exposing a shell cavity between light source 182 and light detector 183 over the base 181. When the light emitted by light source 182 is precluded from reaching light detector 183 by depression of the optional elastomeric cover 184, or by direct insertion of a physical object such as a human foot therebetween, the light detector 183 will establish an electrical continuity condition between leads 185. The necessary power for the light source 182 may be obtained from a battery, or may be connected by electrical leads (not shown) brought from the CONTROL CIRCUIT BOARD 101 (shown in FIG. 2).

Figure 3G:
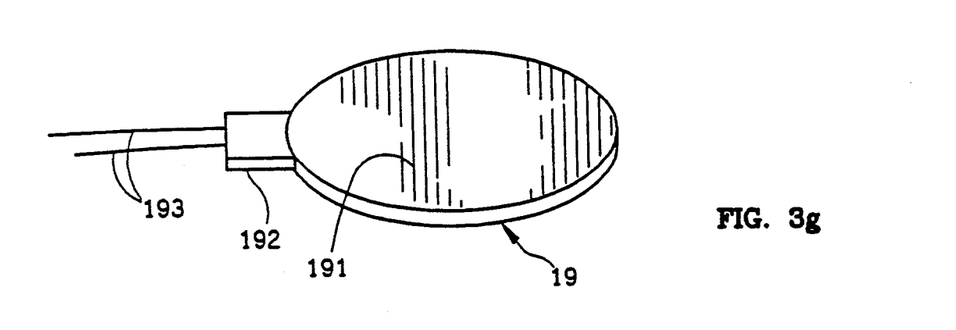

Still another embodiment of a pressure switch SW1-SW4 is shown as pressure switch 19 is perspective view in FIG. 3g. A bladder, or balloon, enclosing either liquid or air is directly pressure-connected to a pressure switch 92. When the bladder 191 is subject to a predetermined pressure, the pressure switch 192 will close, establishing electrical continuity between leads 193.

Figure 3H:
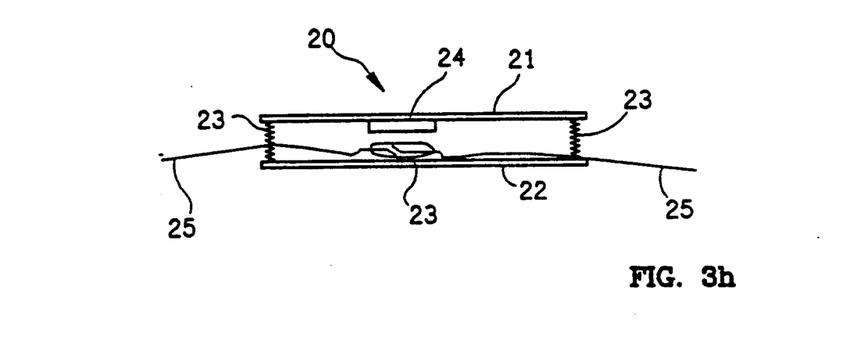

A final embodiment of a pressure switch SW1-SW4 suitable for use in the controller 1 in accordance with the present invention is shown in cross-sectional cut away view in FIG. 3h. Within this pressure switch 20 an upper plate 21 is held at separation from a lower plate 22 by force of springs 23. The upper side of lower plate 22 mounts a reed switch 23. The underside of upper plate 21 mounts a magnet 24. The magnet 24 is normally of sufficient separation from reed switch 23 so that the reed switch 23 is not closed, and so that no electrical continuity exists between electrical leads 25. If, however, a pressure force is exerted between upper member 21 and lower member 22, overcoming the force of springs 23, then the movement of magnet 24 into proximity of reed switch 23 will cause the reed switch 23 to close, establishing electrical continuity between leads 25.

Still other forms of pressure switches are possible. Notably, all the switches shown in FIGS. 3a through 3h will function equivalently in any spatial orientation or position. Accordingly, and in accordance with the principles of the present invention, such switches may be arrayed, and distributed, on any surfaces whatsoever such as floors, walls, and/or ceilings.

Figure 4:
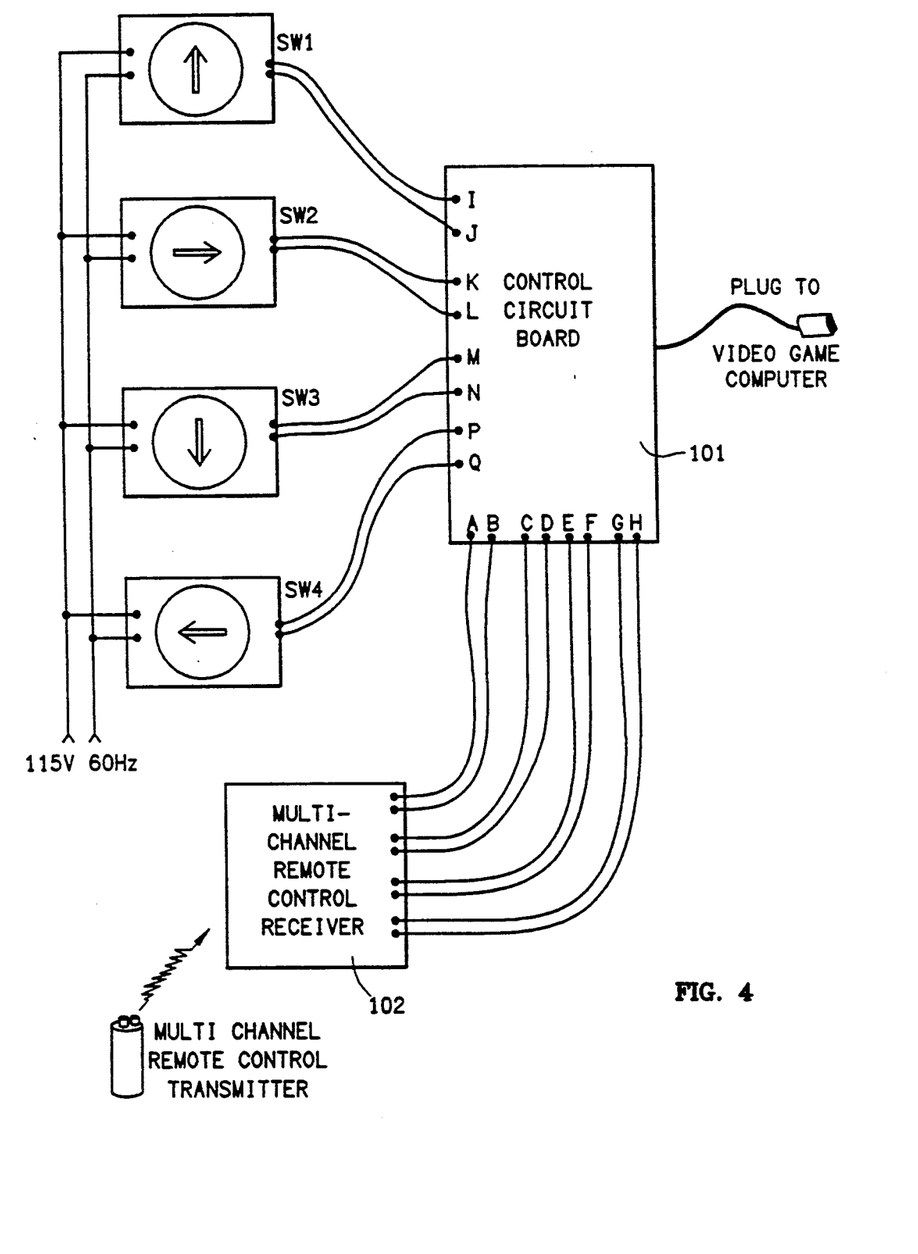
FIG. 4 is a diagrammatic view of a second embodiment of a controller in accordance with the present invention, which second embodiment uses a proximity switch.

An alternative, second, embodiment of the controller 1 in accordance with the present invention using proximity switches PSW1-PSW4 is shown in FIG. 4. The same CONTROL CIRCUIT BOARD 101, and multi-channel remote receiver 102 are used as were used within the first embodiment of the controller 1 shown in FIG. 2. The CONTROL CIRCUIT BOARD 101 still connects to each of the proximity switches PSW1-PSW4 through 2 leads, and senses the actuation of these proximity switches by an electrical continuity between these leads. Unlike the first embodiment of the controller 1 shown in FIG. 2, however, the proximity switches PSW1-PSW4 require a source of power. This power is indicated as 115V 60 Hz to be supplied to each of the proximity switches PSW1-PSW4.

Figure 5:
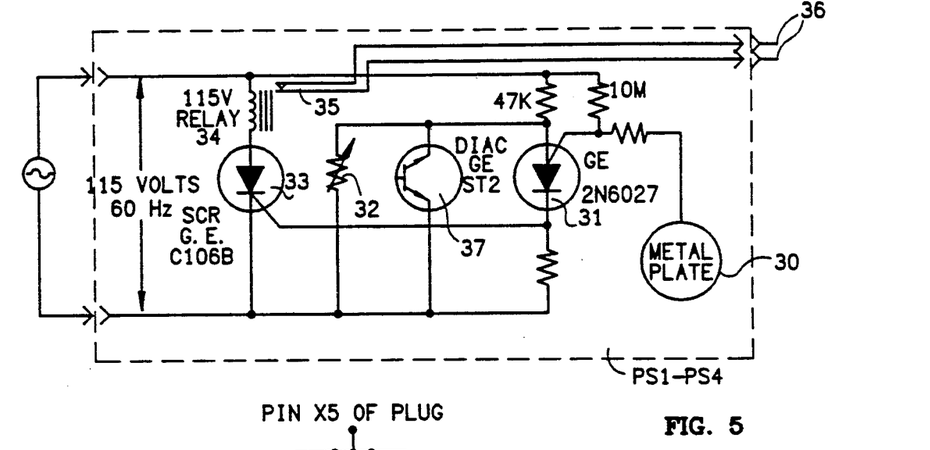
FIG. 5 is a schematic diagram of the proximity switch previously shown in the second controller embodiment diagrammatically illustrated in FIG. 4.

A schematic diagram of a circuit suitable for use within each of the proximity switches PSW1-PSW4 is shown in FIG. 5. A metal plate 30, typically 6" in diameter and disposed toward the human user 4 (shown in FIG. 1) when each of the proximity switches PSW1-PSW4 is disposed for use within the controller 1, is electrically connected to a first TRIAC 31, type GE2N6027. The variable capacitance which will be seen by the metal plate 30 dependent upon whether a human limb, or other object either is, or is not, proximate will serve to trigger the TRIAC 31 is accordance with the threshold level established by adjustment potentiometer 32, typically 1 megohms, and a DIAC 37, GE Part No. ST2. When the TRIAC 31 is enabled to conduct it will, in turn, enable the conduction of silicone control rectifier SCR 33, GE type C106B. The conduction of the SCR will draw current through 115V relay 34, causing a switch 35 to close. It is this selective closure, and continuity, across switch 35 that is seen across output leads 36 which connect to a respective port of CONTROL CIRCUIT BOARD 101 (shown in FIG. 4).

Figure 6:
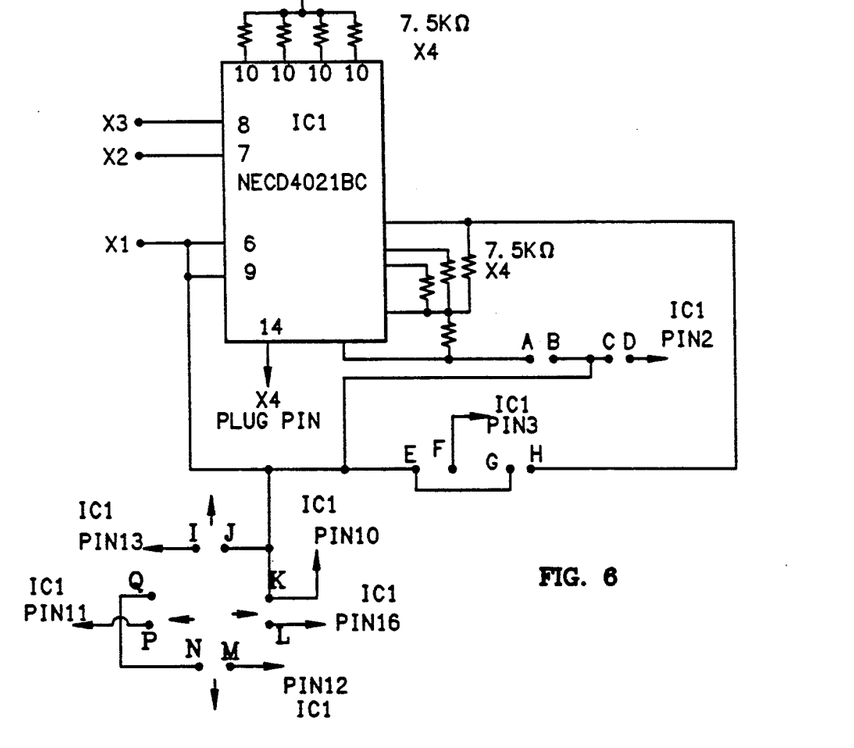
FIG. 6 is a schematic wiring diagram of the control circuit board, previously seen in FIG. 2 and FIG. 4, of both embodiments of a controller in accordance with the present invention.

A schematic diagram of the CONTROL CIRCUIT BOARD 101, previously seen in FIGS. 1, 2, and 4, is shown in FIG. 6. For purposes of clarity, the input signals to such CONTROL CIRCUIT BOARD 101 connected by pairs to terminals A-Q thereof are not positionally localized within the schematic, such as typically to the left hand side of the schematic diagram, while the output signals from the CONTROL CIRCUIT BOARD 101 appearing on pins X1-X5 of plug 104 (shown in FIG. 1 and FIG. 7) are likewise not localized. According to this organization of the schematic of FIG. 6 for functional appreciation, the schematic of FIG. 6 is not readily capable of being enclosed in a box, as is typical, in order to indicate that it is the identical CONTROL CIRCUIT BOARD 101 previously shown in FIGS. 1, 2, and 4. It is, however, the identical CONTROL CIRCUIT BOARD 101 previously shown in FIGS. 1, 2, and 4.

Figure 7A:
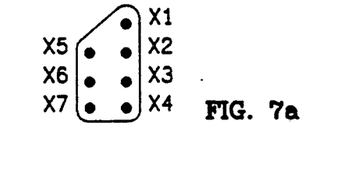
Figure 7B:
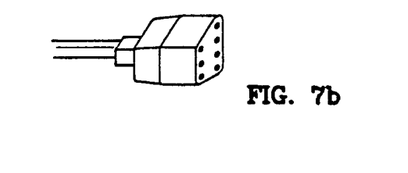

The CONTROL CIRCUIT BOARD 101 shown in FIG. 6 is the same as Nintendo Circuit Board No. TW-8394B-0 used in Nintendo Controller Model No. NES-004. Such a circuit board, and controller, is available from Nintendo of America, Inc., 4820 150th Ave., NE, Redmond, Washington 98052. The schematic diagram is shown in FIG. 6 primarily in order that it may be observed that simple continuity events appearing between any of the pairs of pins AB, CD, . . ., IJ are recognizable by the central integrated circuit, type NECD4021BC, and may be used to provide standard signals, on plug pins X1-X5, to a preexisting standard VIDEO GAME COMPUTER 2 (shown in FIG. 1). The detail wiring of the plug jack with these output signals X1-X5, and unused plug pins X6 and X7, is shown in FIGS. 7a and 7b.

Regardless of the several electrical diagrams within the drawings, the paramount principle of the present invention will be recognized to be embodied in its mechanical spatial array, remote electrical connection, and functional use of selectively adjustable pressure switches, proximity switches, remote control transmitter-receiver pairs, and control circuit boards which are, individually, often conventional in construction. The present invention contemplates a physical spatial partition of these elements which partition is, in the aggregate, both user-selected and flexibly variable. The controller 1 of the present invention is distributed. Alternatively, it may be considered to lack a central housing and/or frame, or to employ a distributed housing and external frame (i.e., the earth, or floor) which is user-established and user-selected.

In particular, each of the pressure switches SW1-SW4, or proximity switches PSW1-PSW4, is completely positioned and located, repositioned and relocated, at variable distances of separation and in any individual patterns and collective orientations, and over any reasonable area, whatsoever. Accordingly, a human user 4 (shown in FIG. 1) positioning such pressure, or proximity switches for the purpose of interacting with a video game computer may do so in accordance with whether he/she desires to make the sense (i.e., up-/down, or left/right) of the actuation of such switches either conventional or unconventional, normal or reversed The user 4 may locate the switches at greater or lesser proximity to each other in accordance with whether he/she is short or tall, or desires to move over small, or large, regions in order to selectively actuate the switches. The user 4 may even selectively establish at each individual switch, at least in some of the switch embodiments, the pressures, or the proximities, which will be required to actuate the switches.

Accordingly, each user of a controller in accordance with the present invention may set up the controller essentially in accordance with his own whims and dictates in matters of the (i) spatial locations, (ii) spatial orientations, and (iii) magnitude of mechanical (pressure) forces that must be selectively applied to the controller in order to sequence the operation of a computer game, or in order to provide progress inputs into an exercise equipment, including an equipment running an exercise videotape. Dependent upon the variable configuration of the controller 1, a single video exercise tape may suffice to induce a strenuous response on the part of a user who is relatively more physically fit, or a less strenuous response on the part of a user who is relatively less physically fit.

Figures 8, 9:
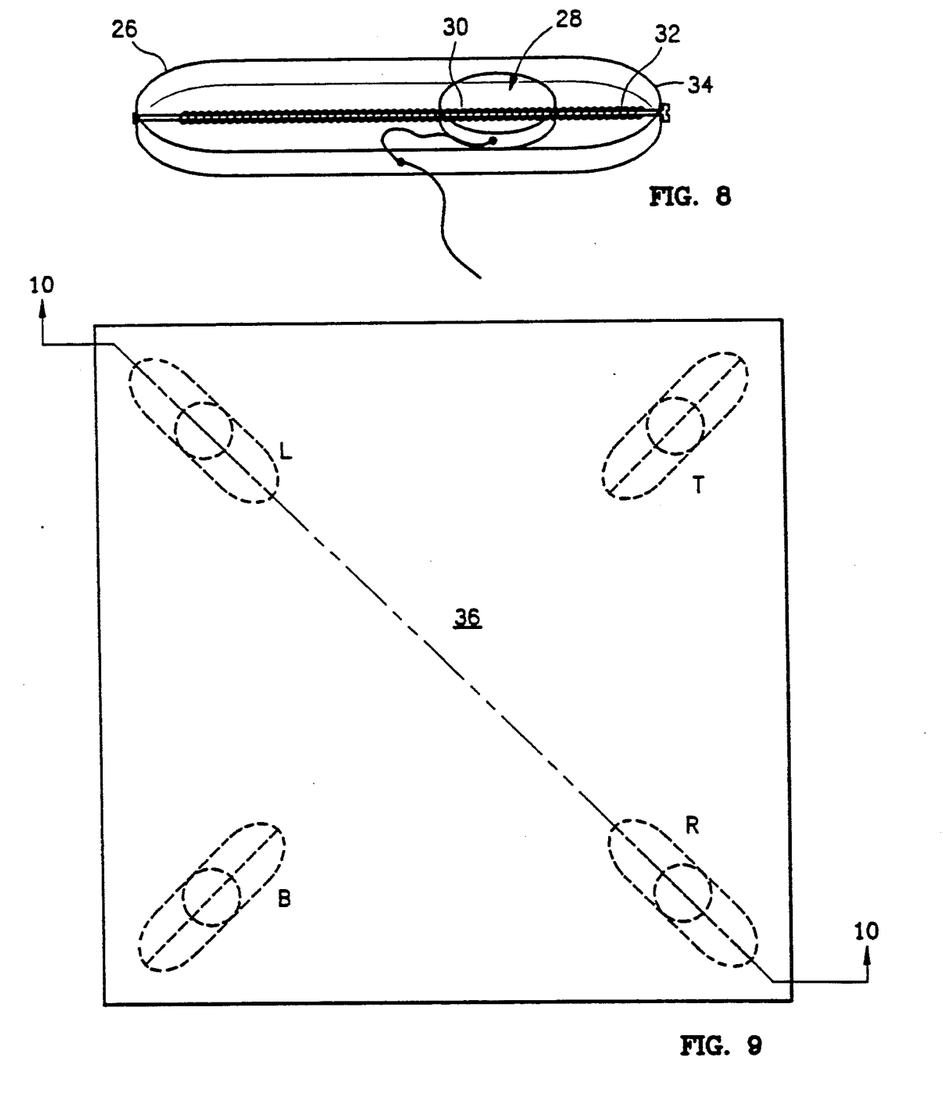
FIG. 8 is a diagrammatic perspective view of a particularly preferable embodiment for housing adjustable pressure and proximity switches usable in video game controllers in accordance with the present invention.
FIG. 9 is a top plan view of a user-selectable controller matrix indicating one arrangement of adjustable switches.

Turning now to FIG. 8, a particularly preferable embodiment of a sensor is an adjustable cartridge 26 containing either a pressure or proximity sensor switch 28 as hereinbefore described and shown in FIGS. 3a–h (14–20). This sensor switch has a centrally located, threaded bore 30 and is engaged by means of a threaded shaft 32 rotatably mounted longitudinally within the walls of an elongated collar 34, which is temporarily placed, or permanently affixed, under a resilient mat or the like. A user may selectively position the switch along its longitudinal axis to suit his/her stride, for example, and maintain a desired degree of difficulty in operation of the switches by turning the screw 32.

FIG. 9 is a top plan view depicting a typical radial arrangement of such sensor cartridges. Four cartridges, containing sensors selected from a group hereinbefore described and depicted in FIGS. 3a–h (14–20), are shown placed beneath a substantially square mat 36, having a relatively flat upper surface on which a human user may suitably stand, and having a lower surface containing a multiplicity of points at which a plurality of sensor housings may be individually attached. Depicted in FIG. 9 is a preferred embodiment showing the longitudinal alignment of each sensor with diagonally opposite corners of the mat, positions T, B, L and R.

The mat can be placed in any orientation, but typically is placed so that sensor T is closest to a viewing monitor. The human user responds to situations presented in the viewing monitor by actuating one or more of the switches with his/her feet. It can readily be seen that increasing the distance between any two switches results in increased travel and concomitant degree of difficulty in responding to the monitor.

Figure 10:
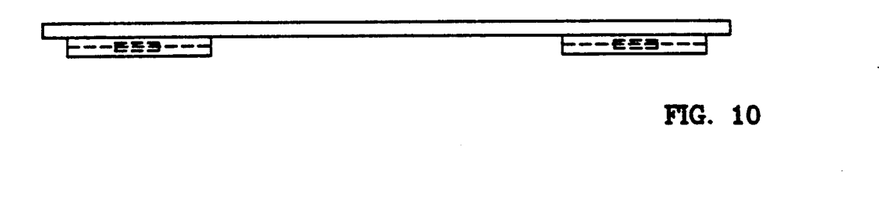
FIG. 10 is a sectional view taken on line 10—10 of FIG. 9.

Attachment of the above-described cartridges is shown in the sectional view in FIG. 10, taken along the line 10—10 of FIG. 9. The cartridges may be temporarily held in place by the weight of the mat, frictional forces between the cartridge, mat and base due to the nature of surfaces in contact, special coatings, velcro, adhesive or the like. The cartridges may also be permanently affixed by connecting means, such as screws, nails, glue or the like.

In accordance with the preceding explanation, still other embodiments of the present invention will suggest themselves to a practitioner of the electronic game apparatus design arts. For example, a controller might be sold for interactive use with a preexisting equipment, such as a stationery exercise equipment, not initially produced for use with a video game, or an exercise videotape. The controller would come with a number of variably locatable, and positionable, switches, that may be variously sensitive to pressure, acceleration, or rotation (speed) of a wheel. The user would position such switches at appropriate physical points on the preexisting exercise equipment. A video tape, or a game, might then be played whereby the user would actuate the exercise equipment, activating the switches, in accordance with the requirements of the game, or tape. By such a sequence a user could transform a generalized, user-configured, video game controller into a ubiquitous controller suitable for sensing diverse physical actuation associated with diverse physical activities, and/or exercise equipments.

In accordance with these and other adaptations and alterations of the present invention, the present invention should be interpreted broadly, in accordance with the following claims, and not solely in accordance with those embodiments within which the invention has been taught.

What is claimed is:

1. A controller electrically interfaced to a video game computer or the like and usable by a human player for the purpose of controlling a progression of a video game or the like, the controller comprising:

a plurality of sensor unit means for individually detecting a presence of a human appendage and for individually producing in response to each such detection an individually-associated detection signal;

a substantially planar matrix for holding each of the plurality of sensor unit means at a position selectable by the human player;

a video game control unit means, located remotely from any one of the plurality of sensor unit means, for receiving the individual detection signals from individual ones of the sensor unit means, and for producing therefrom electrical signals suitable to be received by the video game computer or the like for the purpose of controlling the progression of a video game or the like;

wherein the physical position of individual sensors of the plurality of sensor unit means may be arbitrarily predetermined, at the human's discretion, so that his/her subsequent selective actuation of selective ones of the plurality of sensor unit means with his/her appendage for controlling the progression of the video game or the like may be rendered relatively more or less difficult depending upon the distance of separation, and the area covered, by the sensor unit means' positioning.

2. The controller according to claim 1, wherein the plurality of sensor unit means is organized in an array radiating from a central point of the controller matrix.

3. The controller according to claim 2, wherein the position of individual sensors within the array of sensor unit means may be arbitrarily altered by the human user by variably positioning the sensor within a sensor assembly housing.

4. The controller according to clam 3, wherein the pattern of placement of four sensor assemblies is such that each pair of assemblies is radially aligned through the center point of the matrix, in opposite fashion, along its axis and the line of one pair bisects and lies perpendicularly to the line of the other pair.

5. The controller according to claim 4, wherein each of the radial array of independently activatable sensor assembly means houses an independent moveable sensor unit means.

6. The controller according to claim 5, wherein the distance of separation and the area covered relative to the human player are dependent upon user-determined axial positioning of each individual sensor unit within its housing.

7. A controller electrically interfaced to a video game computer or the like for the purpose of controlling a progression of a video game or the like, the controller comprising:

a platform presenting at its upper surface a relatively flat surface on which a human user may suitably stand, and having and presenting at its lower surface a multiplicity of points at which a plurality of sensor housings may be individually attached;

a like plurality of independently activatable sensor unit means;

a like plurality of sensor unit housings means, attachable to the lower surface of the platform at a plurality of points, for variably retaining the plurality of sensor unit means each at a user-selectable variable location relative to the point of attachment, and a variable distance of separation of one sensor unit means to the next;

a video game control unit means, located remotely from any one of the plurality of sensor unit means, for receiving the individual detection signals from individual ones of the sensor unit means, and for producing therefrom electrical signals suitable to be received by the video game computer or the like for the purpose of controlling the progression of a video game or the like;

wherein the physical position of individual sensors of the plurality of sensor unit means may be arbitrarily predetermined, at the human's discretion, so that his/her subsequent selective actuation of selective ones of the plurality of sensor unit means with his/her appendage for controlling the progression of the video game or the like may be rendered relatively more or less difficult depending upon the distance of separation, and the area covered, by the sensor unit means' positioning.

8. The controller according to claim 7, wherein the platform is a resilient mat.

9. An adjustable sensor cartridge assembly for use with a video game controller comprising:

a sensor having and defining a threaded central bore and actuatable by the presence of a human appendage for producing an electrical signal usable by a video game controller;

an elongated collar, located at a predetermined position relative to a human user, defining a longitudinally extending cavity; and a threaded shaft rotatably mounted in the collar's cavity and meshing with the threads within the bore of the sensor unit;

wherein rotation of the shaft causes the engaged sensor to travel axially along the shaft within the collar's cavity so as to selectively position the sensor within the collar's cavity and relative to the human user.

10. The sensor cartridge according to claim 9, wherein at least one of the plurality of sensor unit means comprises:

a pressure sensor means for detecting a pressure of greater than a threshold level as is producible by force of a human appendage, and for producing an individually-associated detection signal in response to such pressure detection.

11. The sensor cartridge according to claim 9, wherein the sensor unit means comprises:

a proximity sensor means for detecting a spatial proximity of a human appendage, and for producing an individually-associated detection signal in response to such a proximity detection.

* * * * *